US007266460B2

United States Patent
Ammouri et al.

(10) Patent No.: US 7,266,460 B2
(45) Date of Patent: Sep. 4, 2007

(54) NOX SOFTWARE SENSOR

(75) Inventors: Fouad Ammouri, Massy (FR); Thierry Barbe, Lamarche (FR)

(73) Assignee: L'Air Liquide, Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 44 days.

(21) Appl. No.: 10/493,642

(22) PCT Filed: Oct. 4, 2002

(86) PCT No.: PCT/FR02/03393

§ 371 (c)(1),
(2), (4) Date: Apr. 22, 2004

(87) PCT Pub. No.: WO03/034819

PCT Pub. Date: May 1, 2003

(65) Prior Publication Data

US 2004/0249578 A1    Dec. 9, 2004

(30) Foreign Application Priority Data

Oct. 25, 2001    (FR) .................................. 01 13809
Oct. 25, 2001    (FR) .................................. 0113809

(51) Int. Cl.
*G01N 31/00*    (2006.01)
(52) U.S. Cl. ........................ 702/24; 702/130; 702/138
(58) Field of Classification Search ................. 702/24, 702/12, 130, 136, 138, 140
See application file for complete search history.

(56) References Cited

U.S. PATENT DOCUMENTS

| | | | |
|---|---|---|---|
| 5,249,954 A * | 10/1993 | Allen et al. .................... | 431/14 |
| 5,548,528 A | 8/1996 | Havener et al. ............... | 702/22 |
| 6,045,353 A * | 4/2000 | VonDrasek et al. ........... | 431/79 |
| 6,190,160 B1 | 2/2001 | Hibon et al. | |
| 6,244,857 B1 * | 6/2001 | VonDrasek et al. ........... | 431/79 |
| 6,574,613 B1 | 6/2003 | Moreno-Barragan | |
| 2001/0013026 A1 | 8/2001 | Shaffer | |
| 2002/0023044 A1* | 2/2002 | Cichanowicz ................ | 705/37 |

FOREIGN PATENT DOCUMENTS

EP    0 750 192    12/1996

OTHER PUBLICATIONS

Bakal et al.: "*Time delay neural networks for $NO_x$ and CO prediction in fossil fuel plants*", World Congress on Neural Networks, 1995, vol. 3, pp. 111-115.
International Search Report for PCT/FR02/003393 (previously submitted).

* cited by examiner

*Primary Examiner*—John Barlow
*Assistant Examiner*—Anthony Gutierrez
(74) *Attorney, Agent, or Firm*—Christopher J. Cronin; Elwood Haynes

(57) ABSTRACT

Methods and apparatus for determining the NOx content in a combustion flue gas. Several parameters of the combustion process are measured in the combustion furnace. These parameters are then input to a neural network, which then, based upon the input data, generates output data representative of the concentration of NOx in the flue gas. This result is determined without the use of physical NOx sensors.

16 Claims, 5 Drawing Sheets

70 Microcomputer

NOX SOFTWARE SENSOR

BACKGROUND OF THE INVENTION

1. Field of the Invention

The invention relates to the field of the measurement of gas emissions of the NOx type, in particular in industrial processes.

2. Related Art

Numerous industrial processes are based on the combustion of various fuels such as natural gas, LPG etc. Among these processes may be cited in particular second-melt smelting processes or those employed in furnaces for the melting of glass.

The oxidant for these processes, traditionally air, can be enriched with oxygen or even, in certain cases, replaced by oxygen. These processes produce in particular gases such as NOx compounds. The formation of these compounds depends on numerous parameters, which themselves depend on the process (nature of the charge, composition of the oxidant and fuel fluids, burner, pressure of the furnace, etc.).

Ever stricter standards are imposed as regards concern for the environment.

Continuous measurement of these compounds would allow better control of the processes from which they emanate, and/or would make it possible to minimize releases or emissions of NOx so as to comply as far as possible with the standards imposed.

The known methods of measurement can be grouped into two categories: on the one hand in situ measurements, by an appropriate NOx physical sensor and, on the other hand, measurements or estimates by software sensor.

In the example of processes which are conducted in a furnace, the smoke exiting the furnace is often at high temperatures (between 1400° C. and 1600° C.) and is laden with dust. All these conditions therefore affect the operation of the NOx physical sensors which may be installed at the exit of a furnace.

In order to reduce the overly high temperatures of the smoke, recourse is had to a gas conditioning procedure.

Furthermore, measurements made by a physical sensor require frequent calibration as well as technical monitoring of the sensor.

Physical sensors, which are in themselves expensive, are therefore unsuitable for continuous tracking at reasonable cost.

Software sensors are also known, but they do not currently make it possible to attain high accuracy.

In particular, a relative error of estimation of the order of 70% is obtained, which is too large for current needs.

Furthermore, such a sensor requires, in practice, a considerable number of inputs (around 14) and therefore utilizes this many physical sensors to acquire these data. This results in considerable noise in the input data.

Hence, the problem arises of finding a novel process and a novel device for measuring oxides of nitrogen (NOx) in smoke, especially at the furnace exit.

The problem also arises of finding a process and a device giving reliable information regarding the concentration of oxides of nitrogen (NOx) in smoke without performing a direct physical measurement of these oxides of nitrogen.

The problem also arises of finding a sensor allowing continuous measurement, in a reliable manner and with industry-acceptable maintenance, of the emissions of NOx in smoke, in particular at the furnace exit.

The problem furthermore arises of finding a sensor of software type not requiring too large a number of input data.

SUMMARY OF THE INVENTION

The invention relates to a process for measuring the content of NOx compounds (x=1 or 2) contained in smoke produced by combustion.

The invention relates to a process for measuring the NOx content in the smoke produced by combustion in a furnace, characterized in that:
  at least one datum of pressure in the furnace, at least one datum of temperature in the furnace and/or in the smoke resulting from the combustion, and at least one datum representative of the concentration of nitrogen in the smoke are measured as the combustion proceeds,
  these data, or data processed or obtained from these data, are introduced in the guise of input data for a neural network, which delivers at least one output datum representative of the concentration or of the content of NOx in the smoke resulting from the combustion.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
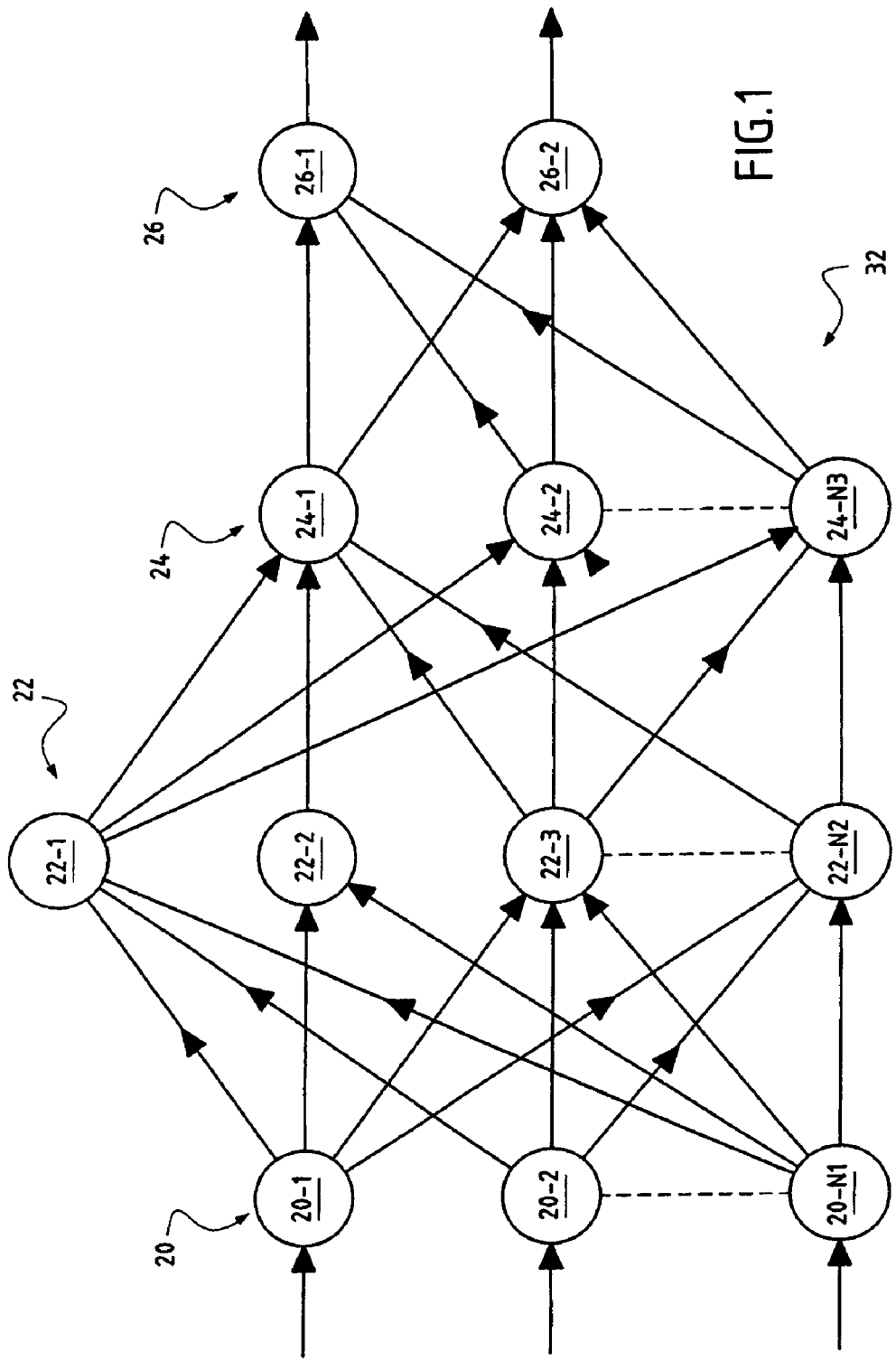
FIG. 1 represents a neural network.

The invention relates to a process for measuring the NOx content in the smoke produced by combustion in a furnace, characterized in that:
  at least one datum of pressure in the furnace, at least one datum of temperature in the furnace and/or in the smoke resulting from the combustion, and at least one datum representative of the concentration of nitrogen in the smoke are measured as the combustion proceeds, and
  these data, or data processed or obtained from these data, are introduced in the guise of input data for a neural network, which delivers at least one output datum representative of the concentration or of the content of NOx in the smoke resulting from the combustion.

According to this process, the measurement does not require any NOx physical sensor, the only measurements performed being those in respect of the input data for the neural network, or else those from which these input data are calculated.

Such a sensor employing a neural network requires neither recalibration nor maintenance.

The estimate of the NOx values is immediate as compared with the measurement of an NOx physical sensor, and the implementation, of the process according to the invention is less expensive than that of a physical sensor.

In the process proposed, only a minimum number of input data are used: a pressure measurement, a temperature measurement and one or two concentration data (carbon dioxide ($CO_2$) and/or the concentration of oxygen ($O_2$), in the smoke) to obtain information regarding the quantity or concentration of nitrogen in the smoke.

The accuracy obtained is furthermore much better than that obtained with the currently known software sensors.

By limiting the input data to 5 or fewer, the noise resulting from too large a number of data is also limited.

The fuel can be a natural gas or else fuel oil or a natural gas and fuel oil mixture.

The oxidant can be oxygen or oxygen-enriched air as oxidant.

According to a particular embodiment, at least two data of pressure in the furnace are measured as the combustion proceeds, these pressure data are processed so as to calculate the mean thereof, and this mean pressure datum is introduced in the guise of input datum for the neural network.

According to another aspect of the invention, at least two data of temperature in the furnace are measured as the combustion proceeds, these temperature data are processed so as to calculate the mean thereof, and this mean temperature datum is introduced in the guise of input datum for the neural network.

Preferably, the measured data exhibit a degree of correlation, with NOx concentration or content data, greater than a predetermined degree.

The processing of the data so as to deliver a datum representative of the NOx content can be carried out continuously, that is to say with a temporal periodicity of the order of a few seconds.

The invention also relates to a device for measuring the NOx content in the smoke produced by combustion in a furnace, characterized in that it includes:
  sensors for measuring at least one datum of pressure in the furnace, at least one datum of temperature in the furnace and/or in the smoke resulting from the combustion, and at least one datum representative of the concentration of nitrogen in the smoke,
  means for or programmed for:
    having the said data processed by a neural network, or for processing at least part of these data to form input data for a neural network and for processing the said data processed by a neural network,
    and for delivering at least one output datum representative of the NOx concentration or content in the smoke resulting from the combustion.

The invention also relates to a combustion system including a burner, a furnace, means for discharging combustion products, and a measurement device as above.

The furnace is for example a glass furnace, or a second-melt rotary smelting furnace, or an incineration furnace.

The invention also relates to a computer program comprising instructions for processing, according to a neural network, at least one datum of pressure of a furnace, at least one datum of temperature in the same furnace and/or in the smoke resulting from combustion occurring in the said furnace, and at least one datum representative of the concentration of nitrogen in the smoke, and for calculating, according to this neural network, at least one output datum representative of the NOx concentration or content in the smoke resulting from the combustion.

The invention also relates to a computer program comprising instructions for:
  processing at least part of the data from at least one datum of pressure of a furnace, at least one datum of temperature in the same furnace and/or in the smoke resulting from combustion occurring in the said furnace, and at least one datum representative of the concentration of nitrogen in the smoke, and for forming input data for a neural network (32),
  calculating, according to this neural network, at least one output datum representative of the NOx concentration or content in the smoke resulting from the combustion.

The invention employs a neural network to carry out a measurement or an estimation of the quantities of oxides of nitrogen produced by a combustion.

A neural network 32 is represented diagrammatically in FIG. 1. The references 20, 22, 24, 26 designate various network layers, including an input layer 20, an output layer 26 and various hidden layers 22, 24.

In FIG. 1 only two hidden layers are represented, but the network may also comprise just one, or more than two. In the case of the present invention, the output layer 26 delivers the quantity of NOx to the user.

Each layer k comprises a certain number of synapses ik (N1 for layer 20, N2 for layer 22, N3 for layer 24, and 2 for the output layer 26).

The input data (processed data) are introduced into the synapses of the input layer.

To each synapse of the neural network there corresponds a nonlinear activation function F, such as a hyperbolic tangent function or a sigmoid function, as well as an activation level.

Moreover, each synapse i of each layer is linked to the synapses j of the next layer, and a weighting Pij weights each link between a synapse i and a synapse j.

This weighting weights the influence of the result of each synapse i in the calculation of the result delivered by each synapse j to which it is linked.

The output Sj from a synapse j is equal to the value of the activation function Fj applied to the weighted sum, by the weights Pij of the synapses, of the results Ai of the activation functions of the synapses i which are connected to it. Stated otherwise:

$$S_j = F_j(^S\!_i Pij \times Ai)$$

The network 32 represented in FIG. 1 is an open network. In a looped network, one of the output data is reused as input datum.

The work entitled "Modélisation, Classification et Commande par Réseaux de Neurones": Méthodologie de Conception et Illustrations Industrielles" [Modelling, Classification and Control using Neural Networks Design Methodology and Industrial Illustrations] by I. Rivals, L. Personnaz, G. Dreyfus, J. L. Ploix (Les Réseaux de Neurones pour la Modélisation et la Commande de Procédés [Neural Networks for Process Modelling and Control], J. P. Corriou, coordinator, Lavoisier Tec et Doc 1995) gives additional information about neural networks.

Physical data, relating to a combustion process which produces NOx compounds, can be measured as such a process is being conducted; these data are then input to the network.

They may be processed beforehand so as to ascertain whether they are relevant, preferably non-redundant, and provide a preferably complete determination of the process.

Relevance means that the information contained in each of the input data contributes to the formation of the result (the NOx content). The mathematical form of this contribution need not be known in order to obtain this result.

Non-redundancy means that the correlations between the selected inputs are small.

Completeness means that all the information required to produce a neural network is present in the suite of data.

The processing of the data with a view to creating a neural network involves acquiring raw or physical data regarding the process. This acquisition preferably covers the entire range over which one wishes the system to be able to predict.

Figure 2:
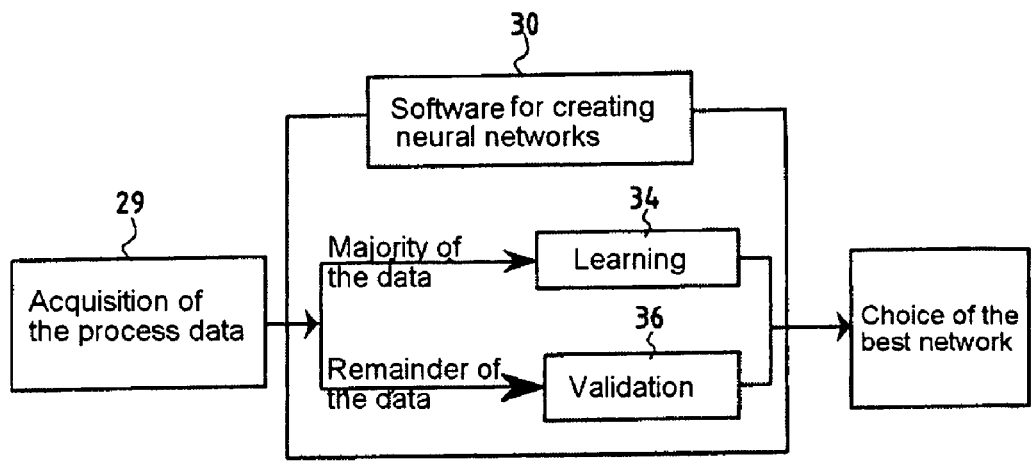
FIG. 2 represents a basic diagram of the creation of a neural network.

Also, and in accordance with the diagram of FIG. 2, raw data are firstly measured (step 29).

These data are then introduced into a piece of software 30 for creating neural networks.

In this software, the majority of the data is used for the learning phase 34, the remainder of the data contributing to the validation of the network (step 36).

The final choice of the best network depends in fact on the objectives fixed. One seeks in fact to obtain the smallest relative deviation, or a predetermined relative deviation, between the measurements (of NOx, these measurements being carried out with the aid of NOx sensors) and the predictions of the network.

Various data processing tools can furthermore be used.

Thus, in the preprocessing phase, it is possible to average or to filter the data with the aim of reducing the acquisition noise.

In the processing phase, a matrix of covariance of the potential inputs for the network can be used so as to limit the redundant data affording the same information.

The input/output correlation vectors can also be used to determine the most influential inputs for the prediction of the said output.

According to the invention, a suite of relevant, non-redundant data ensuring the completeness of the system is the following:
at least one pressure measured in the furnace,
at least one temperature measured in the furnace or in the smoke,
at least one datum representative of the concentration or quantity of nitrogen in the smoke.

By way of example, we may take:
at least one pressure in the furnace,
the temperature of the smoke,
the concentration of CO2 in the smoke,
the concentration of O2 in the smoke.

The quantity of nitrogen in the smoke can be deduced from the concentration of CO2 and of O2 in the smoke: [N2]=1−[CO2]−[O2].

All these data are obtained by measurements with the aid of hardware sensors (pressure sensors, temperature sensors, sensors for measuring concentrations in the smoke).

Measurements of NOx can be obtained with an NOx hardware sensor for a certain duration and with monitoring of an operator.

These raw data are applied to the input layer 20 of the neural network 32, the whole constituting a data set which is sufficient to produce a neural network which can be used in continuous mode.

It is also possible to use other additional data, in particular, so as to increase the accuracy of the result or to increase the rate of convergence of the neural network.

It is for example possible to use a mean pressure in the furnace, instead of a single pressure, this mean resulting from several pressure data obtained by several sensors.

Likewise, it is possible to use a mean temperature in the furnace, instead of or in addition to the temperature in the smoke. This mean temperature then results from several temperature data obtained by several sensors disposed in the furnace.

The network itself can be obtained by implementing neural network production software, such as the NeuroOne software, from the NETRAL company.

The work by I. RIVALS et al. already cited hereinabove gives all the indications for constructing such a neural network. Reference may also be made to the thesis by I. RIVALS, Université Pierre et Marie Curie, 1995, entitled "Modélisation et commande de processus par réseaux de neurones; application au pilotage d'un véhicule autonome" [Process modelling and control by neural networks; application to the steering of an autonomous vehicle].

The user or the designer of the network indicates the following data to this algorithm or to the software used:
number of hidden layers desired,
the form of desired activation function (hyperbolic tangent or sigmoid),
the choice of a looped or open network,
the input data, and corresponding measurements of NOx. These measurements are obtained with an NOx hardware sensor disposed at the stack exit for a certain duration and with monitoring of an operator. Once the network has been constructed and tailored, this NOx hardware sensor is no longer used.

With these data, the software or the algorithm determines the synapses of the neural network and the corresponding weights. More precisely, software is produced in source code or in executable code, which enables the user to obtain NOx concentration data as a function of physical data or raw data measured directly on the process.

If this measurement of raw data is carried out in a continuous or almost continuous manner (that is to say with a period of the order of a few seconds, for example 1 to 5 or to 15 seconds or with a frequency of between 1 Hz and 0.01 Hz), the sensor thus constructed can deliver, continuously or quasi-continuously (with the same period or frequency), a measurement or a signal representative of a measurement of the NOx content produced.

Preferably, for the application to NOx measurements, one chooses a neural network:
with a single hidden layer, the calculation times for a network with two hidden layers or more being too large in the case of a desired period of use of around a few seconds, for example 1 to 5 or to 15 seconds,
static, with no loop.

By way of example, the data processing and the specific modelling of a furnace will be given. This furnace uses pure oxygen as oxidant, natural gas as fuel, and is equipped with a 1 MW burner.

Figure 3:
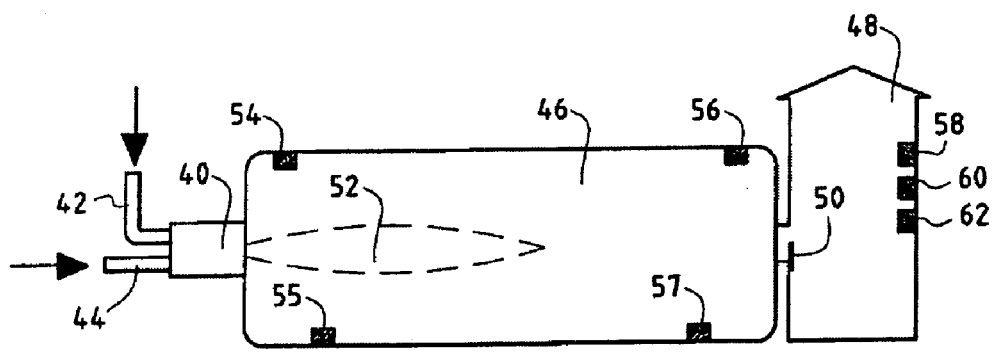
FIG. 3 represents a furnace structure.

Its structure is given diagrammatically in FIG. 3, in which the reference 40 designates the burner itself, supplied via pipes 42 and 44 with fuel and oxidant respectively, and the reference 46 the furnace in which the combustion occurs.

A stack 48 is disposed at the exit of the furnace 46, the opening of a damper 50 making it possible to regulate the pressure in the furnace.

A water circuit system (not represented in the figure) enables energy to be transferred to a charge.

Thermocouples, disposed against the wall of the furnace, on the outside, make it possible to measure the outside temperature of the furnace.

Temperature sensors are disposed in the roof, on the inside of the furnace 46. For example 11 sensors (only two of which are represented) are disposed along the roof, from the entrance of the furnace up to its exit. Thus, a sensor 54 makes it possible to measure the roof temperature, in proximity to the root of the flame 52, whilst a sensor 56 makes it possible to measure the roof temperature, in proximity to the exit of the furnace 46.

Two pressure sensors 55, 57 are also disposed in the furnace.

A temperature sensor 58 can furthermore be disposed in the stack 48, so as to measure the temperature of the smoke. Likewise, sensors 60, 62 make it possible to measure concentrations of CO2 and of oxygen (preferably dry).

A neural network for such a furnace can be constructed with the aid of the NeuroOne software from the NETRAL company. The network is therefore delivered in the form of an executable code.

The physical data measured or the raw data used are: the 2 pressures of the furnace (measured with the aid of the sensors 55 and 57), the percentages of CO2 and of oxygen in the smoke (measured with the aid of the sensor 62), the roof temperatures measured longitudinally in the furnace, the percentage of nitrogen in the fuel, the purity of the oxygen used, the flow rate of oxygen introduced via the pipe 44, the temperature of the smoke (measured with the sensor 58), and the flow rate of fuel introduced via the pipe 42.

Processing of the data makes it possible to:
calculate the mean of the pressures delivered by the sensors 55, 57,
calculate the mean temperature in the furnace, from the temperatures measured by each of the 11 sensors 54, 56.

The 5 data input to the neural network are then:
the mean pressure in the furnace,
the temperature of the smoke,
the concentration of CO2 in the smoke,
the concentration of O2 in the smoke,
the mean temperature in the furnace.

In fact each of these data is preferably considered as an average over a certain time interval, for example as a moving average over an interval of 3 minutes, with an acquisition period which may be 15 s.

A bias is further generated by the software for constructing the neural network.

The network output is preferably threshold, that is to say the NOx concentrations which are below a certain threshold or below a certain predetermined limit value, for example 200 ppm, are disregarded. This is because an NOx value below such a threshold may correspond to a deficiency of one of the sensors and hence be of no interest in the modelling.

Figure 4:
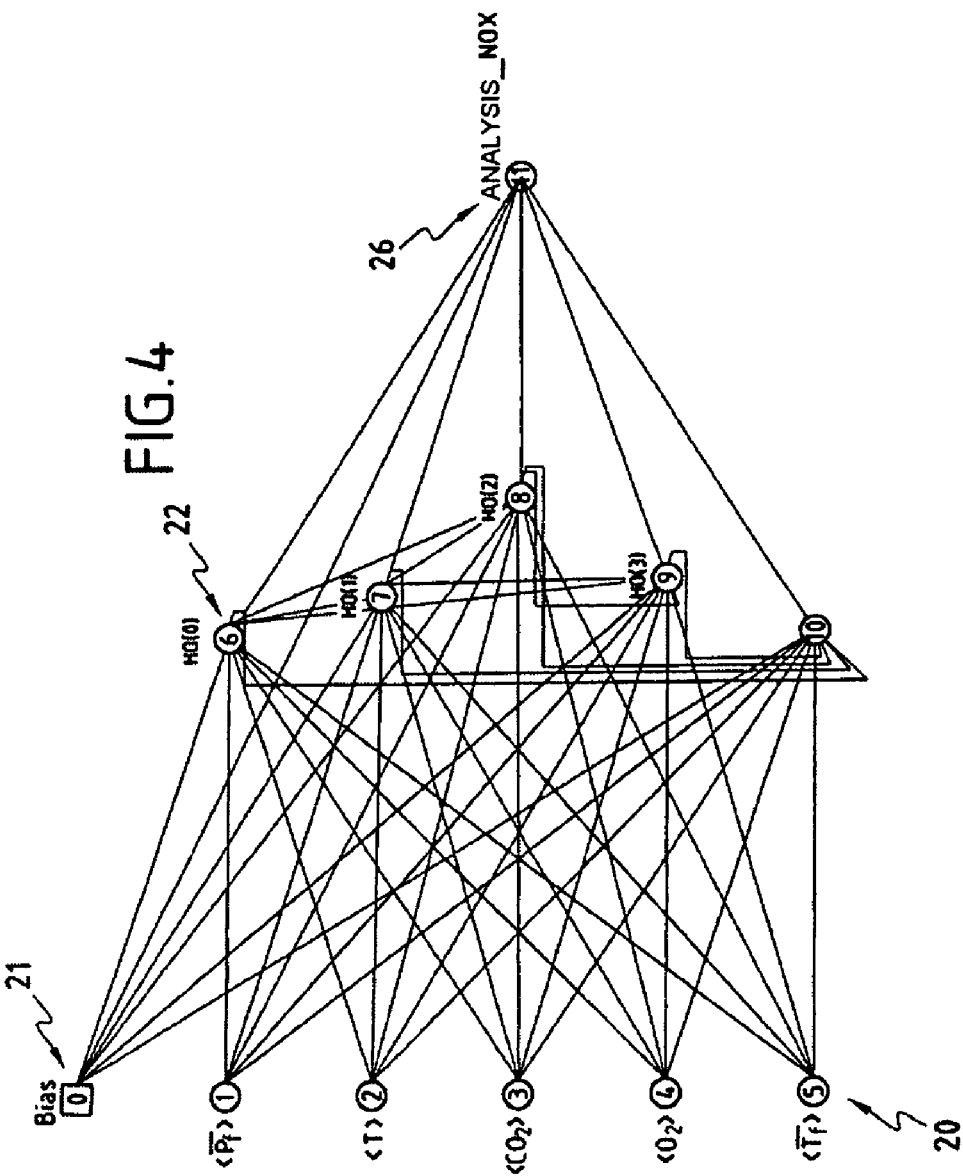
FIG. 4 represents the neural network of a sensor according to the invention.

The structure of the network obtained is represented diagrammatically in FIG. 4. The network comprises just one hidden layer 22. It furthermore comprises the input layer 20 and output layer 26, the reference 21 designating the input bias.

The data are averaged over time, as indicated by the symbol < . . . >. The subscript f relates to the data measured in the furnace. Those for which an average has been produced between several sensors have a bar above them.

Figure 5:
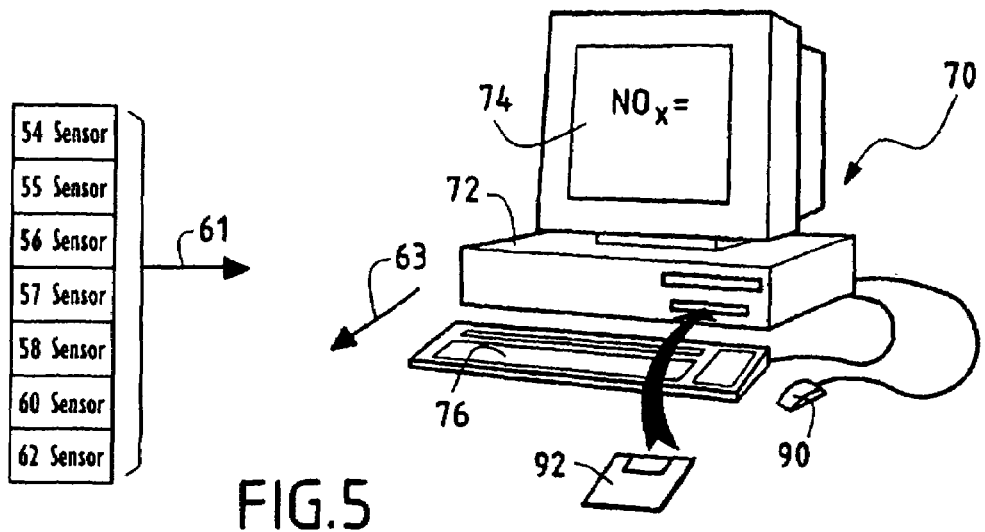
FIG. 5 represents one form of data acquisition and processing means which can be used within the framework of the present invention.
Figure 6:
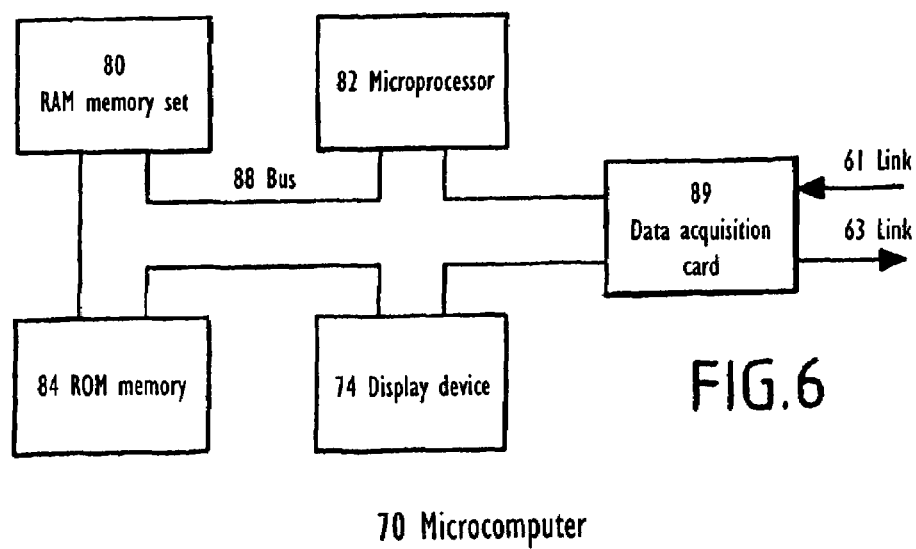
FIG. 6 represents a second form of data acquisition and processing means which can be used within the framework of the present invention.

A system for processing the measurements performed is represented in FIGS. 5 and 6.

Such a system comprises a microcomputer PC 70 to which the data measured by the sensors 54-62 are transmitted via a link 61.

More precisely, the microcomputer 70 comprises (FIG. 6) a microprocessor 82, a set of RAM memories 80 (for storing data), a ROM memory 84 (for storing program instructions).

A data acquisition card 89 transforms the analogue data delivered by the sensors into digital data and puts these data into the format required by the microcomputer. These various elements are linked to a bus 88.

Peripheral devices (screen or display device 74, mouse 90) allow interactive dialogue with a user. In particular, the display means (screen) 74 make it possible to provide a user with a visual indication relating to the calculated NOx content.

Optionally, a link 63 makes it possible to modify certain operating parameters of a combustion process.

Loaded into the microcomputer 70 are the data or the instructions for implementing a processing of the raw or physical data according to the invention, and in particular for performing the prior processing 30 of the raw or directly measured data (see FIG. 2), and for calculating the NOx content with the aid of a neural network 32.

These data or instructions for processing the raw or physical data can be transferred into a memory area of the microcomputer 70 from a diskette or any other medium which can be read by a microcomputer or a computer (for example: hard disk, ROM read only memory, DRAM dynamic random access memory or any other type of RAM memory, compact optical disk, magnetic or optical storage element).

Figure 7:
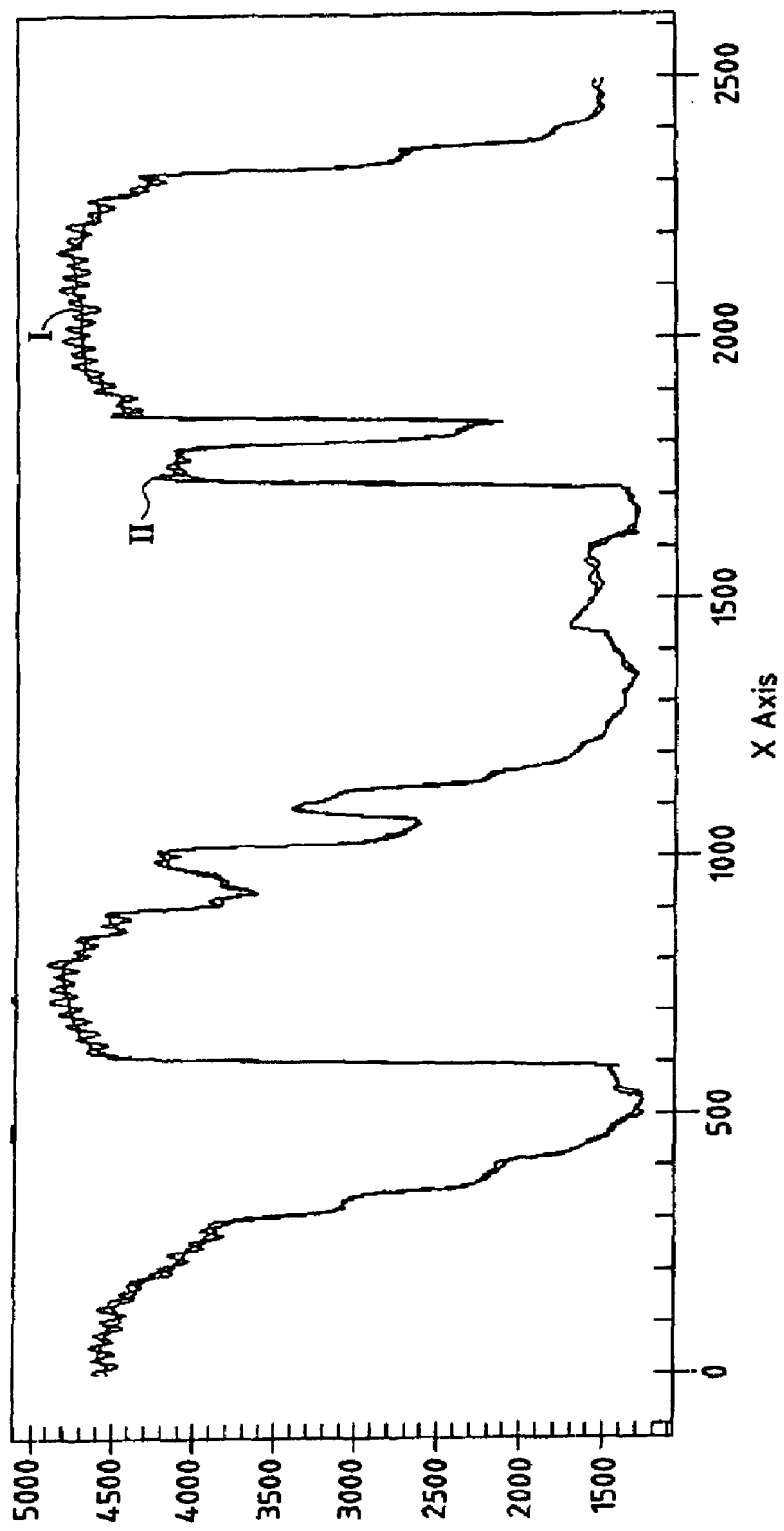
FIG. 7 represents comparative results obtained with the aid of two sensors, one of which is according to the invention.

Comparative results are shown in FIG. 7. Curve I represents the results obtained by modelling and curve II those obtained by measurement with NOx sensors disposed directly in the stack 48 and constantly monitored. As may be noted, modelling allows the best possible approximation to the NOx content since a standard deviation in the relative error of less than 2% between the calculated concentrations and those measured by a physical sensor is obtained. Stated otherwise, 95.45% of the NOx values predicted by the software sensor lie ±4% from the measured value.

Table I gives the standard deviations of the errors in the NOx concentrations obtained with regard to the learning and validation data.

TABLE I

| Type of network | Learning Data | | Validation Data | |
|---|---|---|---|---|
| | Standard Deviation | Relative Standard Deviation | Standard Deviation | Relative Standard Deviation |
| 5 inputs and 5 hidden neurons | 52 ppm | 1.69% | 54 ppm | 1.79% |

The 5 inputs indicated in this example remain valid for other types of burners.

More generally, the software sensor according to the invention is adaptable to all types of furnaces using oxygen-enriched air as oxidant or pure oxygen.

Furthermore, the invention is independent of the control system and accommodates all computer languages, thereby enabling it to be integrated into any control system for existing industrial combustion processes.

An NOx measurement carried out in accordance with the invention can be used in monitoring mode, for example to trigger an alarm as soon as the NOx content oversteps a certain threshold.

It can also be used in a loop for regulating the input parameters of the monitored process. For example, all the input parameters are fixed, bar one, and the nonfixed parameter is regulated in such a way as to maintain the NOx content at a constant value or one lying between two values defining a range of variation. Regulation is performed for example with the aid of the link 63 (see FIG. 5) which transmits the regulating command to the process.

The invention has numerous fields of use. The invention applies in particular to glass furnaces, to second-melt rotary smelting furnaces, to incineration furnaces, to chemical reactors requiring the presence of a flame and whose oxidant is oxygen-enriched air.

According to the invention, a static model is therefore implemented in order to calculate the NOx emissions in various industrial processes, and in particular in the smoke from furnaces using, in the guise of oxidant, oxygen-enriched air or oxygen.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for determining the NOx content in flue gas produced by combustion in a furnace, comprising:
    a) measuring at least one first parameter during the combustion process, said first parameter comprising datum of pressure in said furnace;
    b) measuring at least one second parameter during the combustion process, said second parameter comprising datum of temperature, said temperature datum being measured in the furnace, in the flue gas, or in both the furnace and the flue gas;
    c) measuring at least one third parameter during the combustion process, said third parameter comprising datum representative of the concentration of nitrogen in the flue gas; and
    d) inputting information into a neural network, wherein at least one of said input information is selected from the group consisting:
        i) said first parameter data;
        ii) said second parameter data;
        iii) said third parameter data;
        iv) data processed from said data; and
        v) data obtained from these data;
    e) calculating with said neural network at least one output datum, wherein the output datum is representative of the concentration of NOx in the flue gas resulting from said combustion process; and
    f) receiving the output datum from said neural network.

2. The process according to claim 1, wherein said combustion employs a fuel and an oxidant which comprises oxygen or oxygen-enriched air.

3. The process according to claim 2, wherein said fuel comprises natural gas, fuel oil, or a mixture of natural gas and fuel oil.

4. The process according to claim 2, wherein said third parameter data comprises the measurement of the concentration of carbon dioxide in the flue gas and the concentration of oxygen in said oxidant.

5. The process according to claim 1, wherein at least two first parameter data are measured during the combustion process, the mean value of said first parameter data is calculated, and said mean first parameter value is input as information into said neural network.

6. The process according to claim 1, wherein at least two second parameter data are measured during the combustion process, the mean value of said second parameter data is calculated, and said mean second parameter value is input as information into said neural network.

7. The process according to claim 1, wherein said input information for said neural network comprise fewer than five data points.

8. The process according to claim 1, wherein said input information exhibit a degree of correlation with said NOx content.

9. The process according to claim 8, wherein said degree of correlation is greater than a predetermined threshold value.

10. The process according to claim 1, wherein said neural network comprises a single hidden layer.

11. The process according to claim 1, wherein said neural network is static.

12. The process according to claim 1, wherein said output of said neural network comprises a threshold.

13. The process according to claim 1, wherein the processing of said input information and the delivery of said output data is carried out periodically at a frequency of between about 1 and about 0.01 Hz.

14. An apparatus for determining the NOx content in flue gas produced by combustion in a furnace, comprising:
    a) sensors for measuring at least one first parameter during the combustion process, said first parameter comprising datum of pressure in the furnace;
    b) sensors for measuring at least one second parameter during the combustion process, said second parameter comprising datum of temperature, said temperature datum being measured in the furnace, in the flue gas, or in both the furnace and the flue gas;
    c) sensors for measuring at least one third parameter during the combustion process, said third parameter comprising datum representative of the concentration of nitrogen in the flue gas;
    d) means for having at least part of said first parameter data, said second parameter data, and said third parameter data processed by a neural network to form input data for a neural network;
    e) means for calculating at least one output datum representative of the NOx concentration in the flue gas; and
    f) means for delivering the output datum to a user.

15. A combustion system comprising a burner, a furnace, means for discharging combustion products, and a measurement device, wherein said measurement device comprises:
    a) sensors for measuring at least one first parameter during the combustion process, said first parameter comprising datum of pressure in the furnace;
    b) sensors for measuring at least one second parameter during the combustion process, said second parameter comprising datum of temperature, said temperature datum being measured in the furnace, in the flue gas, or in both the furnace and the flue gas;
    c) sensors for measuring at least one third parameter during the combustion process, said third parameter comprising datum representative of the concentration of nitrogen in the flue gas;
    d) means for having at least part of said first parameter data, said second parameter data, and said third parameter data processed by a neural network to form input data for a neural network;
    e) means for calculating at least one output datum representative of the NOx concentration in the flue gas; and
    f) means for delivering the output datum to a user.

16. The combustion system according to claim 15, wherein said furnace is a glass furnace, a second-melt rotary smelting furnace, or an incineration furnace.

* * * * *